US005688988A

United States Patent [19]

Bosetti et al.

[11] Patent Number: 5,688,988
[45] Date of Patent: Nov. 18, 1997

[54] PROCESS FOR THE PROCUCTION OF AROMATIC URETHANES

[75] Inventors: Aldo Bosetti, Vercelli; Pietro Cesti, Trecate; Emanuele Cauchi, Novara; Ignazio Prestifilippo, Vercelli, all of Italy

[73] Assignee: Ministero dell'Universita' e della Ricerca Scientifica e Technologica, Rome, Italy

[21] Appl. No.: 671,179

[22] Filed: Jun. 27, 1996

[30] Foreign Application Priority Data

Jul. 6, 1995 [IT] Italy ................................ MI95A1446

[51] Int. Cl.$^6$ ................................................ C09C 261/00
[52] U.S. Cl. .............................................................. 560/25
[58] Field of Search .................................................. 560/25

[56] References Cited

U.S. PATENT DOCUMENTS 4,268,684  5/1981  Gurgiolo .

FOREIGN PATENT DOCUMENTS 0 048 371  3/1982  European Pat. Off. .
0 510 459  10/1992  European Pat. Off. .
2 160 111  6/1972  Germany .

*Primary Examiner*—Samuel Barts
*Attorney, Agent, or Firm*—Oblon, Spivak, McClelland, Maier & Neustadt, P.C.

[57] ABSTRACT

A process is described for the preparation of aromatic urethanes in which an organic carbonate in a stoichiometric quantity or in a quantity higher than the stoichiometric value is reacted with an aromatic amine operating in the presence of a carbamation catalyst, wherein this catalyst is selected from zinc and/or copper carbonate hydroxide.

The process gives high yields and selectivity in the useful reaction product.

9 Claims, No Drawings

PROCESS FOR THE PROCUCTION OF AROMATIC URETHANES

The present invention relates to a process for the preparation of aromatic urethanes from an organic carbonate and an aromatic amine in the presence of a carbamation catalyst, wherein said catalyst is selected from zinc and/or copper carbonate hydroxide.

Aromatic urethanes in general, and alkyl N-phenyl urethanes in particular, are valuable intermediates in the production of isocyanates of industrial interest.

Various processes are known in the art for the preparation of urethanes by the reaction of a carbonate and an aromatic amine in the presence of a Lewis acid catalyst. For example, U.S. Pat. No. 3,763,217 describes the preparation of carbamates by the reaction, under reflux conditions, of an alkyl carbonate with an aromatic amine, in the presence of a Lewis acid, preferably uranyl nitrate 1% molar with respect to the amine. Under these conditions the conversion and selectivity yields of the carbamate are about 20%.

U.S. Pat. No. 4,268,684 describes the preparation of urethanes by the reaction of an alkyl carbonate with an aromatic mono- or diamine, using as carbamation catalyst zinc carbonate or zinc oxide active at temperatures of about 200°–300° C.

In particular operating in the presence of 5% in moles of zinc carbonate on the aniline the yield of urethane is about 64.6%; when zinc oxide is used at 10% in moles the yield is equal to 37%.

Operating according to these known processes, when the Lewis acid is used with a low molar ratio with respect to the amine, there is inevitably the formation of substantial quantities of reaction by-products such as ureas or N-alkyl derivatives, even when operating with high molar ratios between carbonate and aromatic amine. Consequently the production of carbamates with good yields requires operating with high contents of catalyst, which is disadvantageous both economically and from the point of view of the separation and purification treatment of the end-products.

In addition, high reaction temperatures tend to further favour the formation of secondary products influencing the conversion and selectivity values in the useful reaction products.

A simple and convenient process has now been found which enables the preparation of aromatic urethanes with practically complete yields and selectivities of the useful reaction product using a zinc and/or copper carbonate hydroxide, as carbamation catalyst.

The present invention is essentially based on the ascertainment that the combination of zinc and/or copper carbonate and hydroxide enables the production of a carbamation catalyst active at temperatures lower than 200° C. and produces high yields and selectivity in the useful reaction product.

In accordance with this, the present invention relates to a process for the preparation of aromatic urethanes by the reaction of an organic carbonate with an aromatic amine operating in the presence of a catalyst, characterized in that said catalyst is a zinc and/or copper carbonate hydroxide having the general formula (I):

$$M_aN_b(OH)_c(CO_3)_d(H_2O)_e \qquad (I)$$

wherein: M and N represent a metal selected from zinc and/or copper; a and b vary from 0 to 4, with the proviso that they are not both 0; c and d vary from 1 to 7; and e has a value varying from 0 to 6.

The catalysts (I) of the present invention can be of natural origin or prepared using the normal synthesis techniques starting from their inorganic salts such as nitrates or chlorides.

Examples of carbamation catalysts suitable for the purposes of the present invention are represented by the following formulae:

$[ZnCO_3 \cdot 2Zn(OH)_2 \cdot H_2O]$; $[ZnCO_3]_3[Zn(OH)_2]_2$; $CuCO_3 \cdot Cu(OH)_2$; $Cu_{1.5}Zn_{3.5}[CO_3]_2[OH]_6$.

Organic carbonates which can be used in the process of the present invention comprise alkyl, aryl or alkyl aryl esters of carbonic acid. The ester group can be an alkyl group with up to 12 carbon atoms, preferably up to 6, or an aryl group with up to 10 carbon atoms.

Examples of organic carbonates particularly suitable for the process of the present invention are cyclic or acyclic carbonates such as for example ethylene carbonate, propylene carbonate, styrene carbonate, dimethyl carbonate, diethyl carbonate, dipropyl carbonate, dibutyl carbonate, diisopropyl carbonate, dihexyl carbonate, methyl butyl carbonate, diphenyl carbonate and methyl phenyl carbonate.

The organic carbonates can be prepared with the conventional methods.

Aromatic amines which can be used in the process of the present invention can be primary or secondary amines, preferably primary amines comprising monoamines, diamines, triamines, etc.

Examples of aromatic amines comprise those represented with the following formulae:

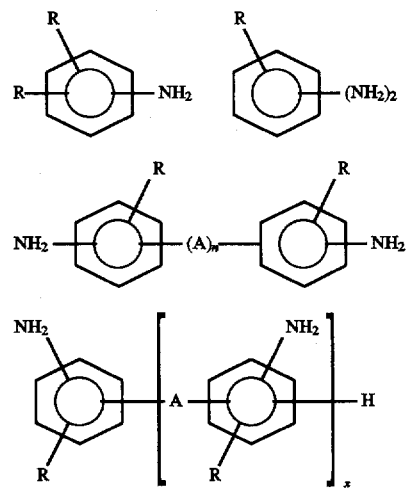

wherein: R is hydrogen, a halogen, or a hyrocarbyl or hydrocarbyloxy group with up to 8, preferably up to 4, carbon atoms, A is a divalent hydrocarbon group with from 1 to 6, preferably from 1 to 4, carbon atoms, n has the value of 0 or 1 and x has a value of between 1 and 6, preferably between 2 and 4.

Aromatic amines which are particularly suitable for the process of the present invention are, for example, aniline, 3,4-dichloro aniline, ortho-, meta- and para-toluidine, 2,4-xylidene, 3,4-xylidine, 2,5-xylidine, 3-propyl aniline, 4-isopropyl aniline, methyl aniline, ethyl aniline, isopropyl aniline, butyl amine, heptyl amine, 4,4'-diamino-diphenyl methane, 2,4,4'-triamino diphenyl ether, 2,6-diamino naphthalene, 4,4'bismethylene diphenylamine, 4,4'-methylenedianiline.

Examples of aromatic urethanes which can be prepared with the process of the present invention are:

N-methylphenylurethane, N-butylphenylurethane, N-pentylphenylurethane, N-hexylphenylurethane, 4,4'-methylenedimethyldiphenylurethane.

The carbonate and amine are interacted in the presence of the catalyst to produce the desired aromatic urethanes.

The quantity of catalyst used in the reaction can vary from 20 to 0.5% in moles, preferably from 15 to 1.0% in moles, with respect to the amine.

To obtain a complete conversion of the amine to urethane, the carbonate must generally be present in at least an equivalent stoichiometric ratio. The carbonate is preferably used in excess with respect to the amine to minimize side-reactions such as the formation of urea. It is advantageous to use a molar ratio between carbonate and amine of between 30/1 and 1/1, preferably between 10/1 and 5/1.

The reaction temperatures can conveniently vary from 100° to 190° C. Temperatures of about 140°–180° C. are preferably used.

Operating under the above conditions a complete conversion of the amine is generally obtained in times of about 1–30 hours.

The carbamation reaction can be carried out in a stainless steel pressure-resistant reactor. The operating pressure is that obtained by boiling the solvent and the amine.

At the end of the reaction the urethane contained in the mixture is isolated and purified. The operations are conveniently carried out in two phases i.e. removal of the residual carbonate and purification of the urethane. The removal of the carbonate is carried out by evaporation of the reaction mixture. In practice at the end of the reaction the pressure of the system is slowly lowered, bringing the temperature at the bottom to 110° C., preferably to about 100° C., and maintaining these conditions while the carbonate is distilled until it has been completely removed. The urethane is then distilled at a further reduced pressure.

The process of the present invention has the advantage of transforming the amine into the relative urethane with practically total yields, using reduced quantities of catalyst and bland operating conditions. There are obvious economical advantages of the process, including improved specifications as regards consumption of catalyst and amine.

The following experimental examples are illustrative but do not limit the scope of the present invention.

EXAMPLE 1

9.2 g (0.099 moles) of aniline, 43.8 g (0.486 moles) of dimethylcarbonate and 2.2 g (0.0064 moles; 6% in moles with respect to the aniline) of zinc carbonate hydroxide hydrate [$ZnCO_3 \cdot 2Zn(OH)_2 \cdot H_2O$] are charged into a cylindrical steel pressure-resistant reactor with a useful volume of 100 ml. After charging, the reactor is immersed in an oil-bath thermostat-regulated at 160° C. and magnetically stirred at about 300 rpm. The reaction is carried out at a pressure of 8 atms ($P_{max}$) for 5 hours. After cooling, the raw reaction product is analyzed via HPLC (RP-18 column, eluant water/acetonitrile 60/40, v/v, flow 1.5 ml/minute) obtaining:

| aniline | 0.5% |
|---|---|
| phenylmethylurethane | 97.5% |
| diphenylurea | 0.5% |
| N-methylaniline | 1.0% |

From these results it is possible to calculate the following conversion and selectivity values:

conversion 99.5% with respect to the aniline, selectivity 98% per mole with respect to the phenyl methylurethane.

yield 97.5% with respect to the aniline.

After purifying the raw product by chromatography with a silica gel column, eluant hexane/ethyl acetate (90/10, v/v) the following products are obtained:

| phenylmethylurethane | 14.2 g |
|---|---|
| diphenylurea | 0.51 g |
| yield 95% with respect to the initial aniline. | |

EXAMPLE 2

The same procedure is carried out as in example 1, using 1.1 g (0.0032 moles; 3% in moles) of catalyst. After 18 hours the raw product is analyzed by HPLC obtaining:

| aniline | 0.6% |
|---|---|
| phenylmethylurethane | 97.5% |
| diphenylurea | 0.5% |
| N-methylaniline | 0.9% |

From these results it is possible to calculate the following conversion and selectivity values:

conversion 99.4% with respect to the aniline, selectivity 98% per mole with respect to the phenylmethylurethane.

yield 97.4%

After purification the following products are obtained:

| phenylmethylurethane | 14.0 g |
|---|---|
| diphenyl urea | 0.5 g |
| yield 94% with respect to the initial aniline. | |

EXAMPLE 3

The same procedure is carried out as in example 1, carrying out the reaction at 140° C. and at a pressure of 6 atms. After 19 hours the raw product is analyzed via HPLC obtaining:

| aniline | 0.4% |
|---|---|
| phenylmethylurethane | 97.5% |
| diphenylurea | 0.7% |
| N-methylaniline | 1.4% |

From these results it is possible to calculate the following conversion and selectivity values:

conversion $\geq$99% with respect to the initial aniline, selectivity 98% per mole with respect to the phenylmethylurethane yield 97%

After purification the following products are obtained:

| phenylmethylurethane | 14.2 g |
|---|---|
| diphenylurea | 0.57 g |
| yield 95% with respect to the initial aniline. | |

EXAMPLE 4

9.2 g (0.099 moles) of aniline, 43.8 g (0.486 moles) of dimethylcarbonate and 1.8 g (0.0052 moles; 5% in moles with respect to the aniline) of zinc carbonate hydroxide hydrate are charged into a cylindrical steel pressure-resistant reactor with a useful volume of 100 ml. After charging, the reactor is immersed in an oil-bath thermostat-regulated at 180° C. and magnetically stirred at about 300 rpm. The reaction is carried out for 30 minutes at a pressure of 8 atms ($P_{max}$). After cooling, the raw reaction product is analyzed obtaining:

| | |
|---|---|
| aniline | 75% |
| phenylmethylurethane | 24.2% |
| N-methylaniline | 0.8% |

From these results it is possible to calculate the following conversion and selectivity values:

conversion 25% with respect to the aniline, selectivity 97% per mole with respect to the phenylmethylurethane.

yield 24%

After purification the following products are obtained:

| | |
|---|---|
| phenylmethylurethane | 3.58 g |
| non-reacted aniline | 6.83 g |
| yield 24% with respect to the initial aniline. | |

EXAMPLE 5

The same procedure is carried out as in example 1, using 1.6 g (0.0081 moles) of 4,4'-methylenedianiline (MDA), 8 g (0.089 moles) of dimethylcarbonate and 0.36 g (0.001 moles, 13% in moles with respect to the MDA) of catalyst. The reaction is carried out for 6 hours at a pressure of 4.5 atms. After cooling the raw reaction product is analyzed via HPLC obtaining:

| | |
|---|---|
| 4,4'-methylenedianiline | 0.7% |
| 4,4'-methylenediphenylurethane | 73.0% |
| N-methylenedianiline | 26.3% |

From these results it is possible to calculate the following conversion and selectivity values:

conversion 99% with respect to the 4,4'-MDA selectivity 73% per mole with respect to the 4,4'methylenemethyldiphenylurethane.

yield 73%

After purification the following products are obtained:

| | |
|---|---|
| 4,4'methylenedimethyldiphenylurethane | 1.85 g |
| N-methylmethylenedianiline (mixture of isomers) | 0.4 g |
| yield 72.5% with respect to the initial 4,4'-MDA. | |

EXAMPLE 6

(Comparative)

The same procedure is carried out as in example 3, using as catalyst 0.94 g (0.009 moles, 9% in moles) of zinc hydroxide. After 19 hours the raw reaction product is analyzed obtaining:

| | |
|---|---|
| aniline | 96.0% |
| phenylmethylurethane | 2.2% |
| N-methylaniline | 0.8% |
| diphenylurea | 0.8% |

From these results it is possible to calculate the following conversion and selectivity values:

conversion 4% with respect to the aniline, selectivity 55% per mole with respect to the phenylmethylurethane.

yield 2.2%

EXAMPLE 7

(Comparative)

The same procedure is used as described in example 4, using 5 g (0.0537 moles) of aniline, 25 g (0.2775 moles) of dimethylcarbonate and 0.314 g (0.0025 moles; 5% in moles) of zinc carbonate. After 0.5 hours at 180° C. the raw reaction product is analyzed obtaining:

| | |
|---|---|
| phenylmethylurethane | 4.3% |
| N-methylaniline | 4.5% |
| diphenylurea | 1.3% |
| aniline | 90% |

From these results it is possible to calculate the following conversion and selectivity values:

conversion 10% with respect to the aniline, selectivity 43% per mole with respect to the phenylmethylurethane.

yield 4.3% with respect to the initial aniline.

EXAMPLE 8

The same procedure is used as in example 1, using 1.95 g (0.0034 moles, 3% in moles) of anhydrous zinc carbonate hydroxide $[ZnCO_3]_3[Zn(OH)_2]_2$. After 10 hours the raw reaction product is analyzed obtaining:

| | |
|---|---|
| aniline | 3.7% |
| phenylmethylurethane | 93.0% |
| N-methylaniline | 2.2% |
| diphenylurea | 1.1% |

From these results it is possible to calculate the following conversion and selectivity values:

conversion 96.3% with respect to the aniline, selectivity 96.5% per mole with respect to the phenylmethylurethane.

yield 93%

After purification the following products are obtained:

| | |
|---|---|
| phenylmethylurethane | 13.7 g |
| diphenylurea | 0.5 g |
| aniline | 0.033 g |
| N-methylaniline | 0.10 g |
| yield 91.6% with respect to the initial aniline. | |

Table 1 summarizes the data obtained in examples 1–8.

TABLE 1

| Ex. | Catalyst (mole %) | T °C. | time hrs | P atm | Conversion % | Selectivity % |
|---|---|---|---|---|---|---|
| 1 | 6 | 160 | 5 | 8 | 99.5 | 98 |
| 2 | 3 | 160 | 18 | 8 | 99.4 | 98 |
| 3 | 6 | 140 | 19 | 6 | ≧99 | 98 |
| 4 | 5 | 180 | 0.5 | 8 | 25 | 97 |
| 5 | 13 | 170 | 6 | 4.5 | 99.3 | 73.5 |
| 6 | 9 | 140 | 19 | 6 | 4 | 55 |
| 7 | 5 | 180 | 0.5 | 8 | 10 | 43 |
| 8 | 3 | 160 | 10 | 8 | 96.3 | 96.5 |

EXAMPLE 9

The same procedure is used as in example 1, using 1.17 g (0.0053 moles, 5% in moles) of copper carbonate hydroxide $CuCO_3Cu(OH)_2$.
After 10 hours the raw reaction product is analyzed obtaining:

| | |
|---|---|
| aniline | 47.0% |
| phenylmethylurethane | 44.5% |
| N-methylaniline | 5.0% |
| diphenylurea | 3.5% |

From these results it is possible to calculate the following conversion and selectivity values:

conversion 53% with respect to the aniline, selectivity 84% per mole with respect to the phenyl methylurethane.

yield 44.5%

After purification the following products are obtained:

| | |
|---|---|
| phenylmethylurethane | 6.45 g |
| diphenylurea | 0.65 g |
| aniline | 4.2 g |
| N-methylaniline | 0.54 g |
| yield 43% with respect to the initial aniline. | |

EXAMPLE 10

The same procedure is used as in example 1, using 3.13 g (0.0064 moles, 6% in moles) of zinc and copper carbonate hydroxide $Cu_{1.5}Zn_{3.5}[CO_3]_2(OH)_6$. After 5 hours the raw reaction product is analyzed obtaining:

| | |
|---|---|
| aniline | 0.8% |
| phenylmethylurethane | 97.5% |
| N-methylaniline | 0.8% |
| diphenylurea | 0.8% |

From these results it is possible to calculate the following conversion and selectivity values:

conversion 99% with respect to the aniline, selectivity 98.5% per mole with respect to the phenyl methylurethane.

yield 97%

After purification the following products are obtained:

| | |
|---|---|
| phenylmethylurethane | 14.2 g |
| diphenylurea | 0.11 g |
| N-methylaniline | 0.15 g |
| yield 95% with respect to the initial aniline. | |

We claim:

1. A process for the preparation of aromatic urethanes by the reaction of an organic carbonate with an aromatic amine operating in the presence of a catalyst, characterized in that said catalyst is a zinc and/or copper carbonate hydroxide having the general formula (I):

$$M_aN_b(OH)_c(CO_3)_d(H_2O)_e \qquad (I)$$

wherein: M and N represent a metal selected from zinc and/or copper; a and b vary from 0 to 4, with a proviso that they are not both 0; c and d vary from 1 to 7; and e has a value varying from 0 to 6.

2. The process according to claim 1, characterized in that the organic carbonate is selected from ethylene carbonate, propylene carbonate, styrene carbonate, dimethyl carbonate, diethyl carbonate, dipropyl carbonate, dibutyl carbonate, diisopropyl carbonate, dihexyl carbonate, methyl butyl carbonate, diphenyl carbonate and methyl phenyl carbonate.

3. The process according to claim 1, characterized in that the aromatic amine is selected from: aniline, 3,4-dichloro aniline, ortho-, meta- and para-toluidine, 2,4-xylidene, 3,4-xylidine, 2,5-xylidine, 3-propyl aniline, 4-isopropyl aniline, methyl aniline, ethylaniline, isopropyl aniline, butyl amine, heptyl amine, 4,4'-diamino-diphenyl methane, 2,4,4'-triamino diphenyl ether, 2,6-diamino naphthalene, 4,4'bismethylene diphenylamine, 4,4'-methylenedianiline.

4. The process according to claim 1, characterized in that the molar ratio between the organic carbonate and the aromatic amine is between 30/1 and 1/1.

5. The process according to claim 4, characterized in that the molar ratio between the organic carbonate and aromatic amine is between 10/1 and 5/1.

6. The process according to claim 1, characterized in that a quantity of catalyst having general formula (I) of between 20% and 0.5% per mole of amine, is used.

7. The process according to claim 6, characterized in that the quantity of catalyst is between 15 and 1.0% in moles per mole of amine.

8. The process according to claim 1, characterized in that the operating temperatures are between 100° and 190° C.

9. The process according to claim 8, characterized in that the temperatures are between 140° and 180° C.

* * * * *

UNITED STATES PATENT AND TRADEMARK OFFICE
CERTIFICATE OF CORRECTION

PATENT NO.  : 5,688,988
DATED       : November 18, 1997
INVENTOR(S) : Aldo BOSETTI et al.

It is certified that error appears in the above-identified patent and that said Letters Patent is hereby corrected as shown below:

On the title page, Item [54], the Title should read:

-- PROCESS FOR THE PRODUCTION OF AROMATIC URETHANES --

On the title page, Item [73], the Assignee should read:

-- Ministero dell'Universita' e della Ricerca Scientifica e Tecnologica. Rome Italy --

Signed and Sealed this

Third Day of February, 1998

*Attest:*

BRUCE LEHMAN

*Attesting Officer*

*Commissioner of Patents and Trademarks*